(12) United States Patent
Warner et al.

(10) Patent No.: US 10,556,085 B2
(45) Date of Patent: *Feb. 11, 2020

(54) HEAT-MOISTURE EXCHANGER WITH AEROSOL BYPASS

(71) Applicants: Christopher D. Warner, Apopka, FL (US); James V. Waldo, Jr., Tampa, FL (US)

(72) Inventors: Christopher D. Warner, Apopka, FL (US); James V. Waldo, Jr., Tampa, FL (US)

(*) Notice: Subject to any disclaimer, the term of this patent is extended or adjusted under 35 U.S.C. 154(b) by 577 days.

This patent is subject to a terminal disclaimer.

(21) Appl. No.: 15/241,380

(22) Filed: Aug. 19, 2016

(65) Prior Publication Data

US 2018/0050168 A1 Feb. 22, 2018

(51) Int. Cl.
| *A61M 16/22* | (2006.01) |
| *A61M 16/10* | (2006.01) |
| *A61M 16/08* | (2006.01) |
| *A61M 15/00* | (2006.01) |
| *A62B 9/00* | (2006.01) |

(52) U.S. Cl.
CPC .... *A61M 16/1045* (2013.01); *A61M 16/0816* (2013.01); *A61M 16/105* (2013.01); *A61M 15/009* (2013.01); *A61M 16/085* (2014.02); *A62B 9/003* (2013.01)

(58) Field of Classification Search
CPC .. A61M 11/00; A61M 15/00; A61M 15/0065; A61M 15/009; A61M 16/01; A61M 16/08; A61M 16/0808; A61M 16/0816; A61M 16/085; A61M 16/104; A61M 16/1045; A61M 16/1055; A61M 16/106; A61M 16/107; A61M 16/16; A61M 16/20; A61M 16/22; A61M 2230/432; A62B 9/003; Y10S 128/909; Y10S 128/911; Y10S 128/912

See application file for complete search history.

(56) References Cited

U.S. PATENT DOCUMENTS

| 4,497,361 | A | * | 2/1985 | Hajicek | F24F 3/1423 165/10 |
| 6,550,476 | B1 | | 4/2003 | Ryder | |
| 6,588,421 | B1 | * | 7/2003 | Diehl | A61M 16/12 128/201.13 |
| 6,792,943 | B2 | | 9/2004 | Kumar et al. | |

(Continued)

*Primary Examiner* — Annette Dixon
(74) *Attorney, Agent, or Firm* — FisherBroyles LLP; Anthony Dovale

(57) ABSTRACT

A heat-moisture exchanger device for use with a patient ventilator circuit is provided. A rotatable central element is positioned in a housing, and a filter is coupled to the rotatable central element. A first conduit can allow fluid to enter or exit a chamber of the housing and a second conduit on an opposed surface can allow fluid to enter or exit the chamber. A third conduit on the rotatable central element can selectively place the first conduit in sealed fluid communication with the second conduit when the rotatable central element is in a first position. Alternatively, the rotatable central element can be rotated to a second position in which the third conduit does not place the first conduit in sealed fluid communication with the second conduit, and any fluid flowing through the chamber must pass through the filter.

17 Claims, 4 Drawing Sheets

(56) References Cited

U.S. PATENT DOCUMENTS

| | | | |
|---|---|---|---|
| 6,792,946 B1 * | 9/2004 | Waldo, Jr. ......... | A61M 16/1045 128/201.13 |
| 7,069,928 B1 * | 7/2006 | Waldo, Jr. ......... | A61M 16/1045 128/201.13 |
| 9,737,679 B2 * | 8/2017 | Ritter, III .......... | A61M 16/0816 |

* cited by examiner

HEAT-MOISTURE EXCHANGER WITH AEROSOL BYPASS

FIELD OF THE INVENTION

This invention relates generally to a patient heat-moisture exchanger attached to a nebulizer circuit. More particularly, it refers to a heat-moisture exchanger attached to a patient ventilator circuit, which includes a metered dose inhaler, the exchanger permitting medicament to pass through the heat moisture exchanger without passing through internally mounted filters and without disconnection from the ventilator circuit.

BACKGROUND OF THE INVENTION

A heat-moisture exchanger attached to a nebulization device is described in U.S. Pat. No. 6,550,476. This device has a rotatable second housing connected to a first housing. The first housing has at least two chambers enclosing an absorbent material and providing a passageway for an aerosol. The second housing encloses the nebulizer. Valves control the primary gas flow through a passageway to bypass the absorbent material. This device maintains the continuity of a closed ventilator circuit when administering an aerosolized medication to prevent interruption of ventilation to a patient. However, the device is complex and expensive to produce. A simpler device is needed to maintain the continuity of a closed ventilator circuit when administering an aerosolized medication to a patient connected to a ventilation system.

U.S. Pat. No. 6,792,946 described a simplified way of maintaining the continuity of a closed ventilator circuit with two separate heat-moisture exchange materials. What is needed is a less expensive and easier way of achieving the same result.

SUMMARY

Presented herein are methods, devices and systems for maintaining the continuity of a closed ventilator circuit when administering an aerosolized medication to a patient. A heat-moisture exchanger device for use with a patient ventilator circuit is provided. In one aspect, the heat-moisture exchanger device comprises at least one of a housing, a rotatable central element positioned in the housing, and a filter coupled to the rotatable central element.

In one aspect, the housing comprises a first wall, an opposed second wall and sidewall extending between the first wall and the second wall to form a chamber. A first conduit can be positioned thereon an outer surface of the first wall, and a first passageway can be defined through the first conduit and the first wall, according to one aspect. In another aspect, a second conduit can be positioned thereon an outer surface of the second wall, and a second passageway can be defined through the second conduit and the second wall. In still another aspect, a longitudinal axis of the first conduit and a longitudinal axis of the second conduit can be substantially aligned.

The rotatable central element can be positioned therein the chamber of the housing. In one aspect, the rotatable central element comprises a body having an outer edge. In another aspect, the out edge of the body can be sized and shaped to conform to an inner surface of the sidewall of the housing. A third conduit having a longitudinal axis can be positioned thereon the body such that the third conduit extends from a first side of the body to a second side of the body. In one aspect, a third passageway can be defined through the third conduit.

In use, the rotatable central element can be rotatable about and between a first position, in which the longitudinal axis of the third conduit is substantially aligned with the longitudinal axis of the first conduit and the longitudinal axis of the second conduit, and a second position, in which the longitudinal axis of the third conduit is not aligned with the longitudinal axis of the first conduit and the longitudinal axis of the second conduit. In the first position, medication can be supplied to the patient ventilation circuit without requiring the medication to pass through turns or past obstructions such as fan blades and the like. Instead, the medication can pass smoothly through the first, second and third passageways when the passageways are aligned. In the second position, fluid passing through the heat-moisture exchanger device must pass through the filter because of the misalignment of the third passageway relative to the first and second passageways.

Related methods of operation are also provided. Other apparatuses, methods, systems, features, and advantages of the heat-moisture exchanger device and the method of its use will be or become apparent to one with skill in the art upon examination of the following figures and detailed description. It is intended that all such additional apparatuses, methods, systems, features, and advantages be included within this description, be within the scope of the heat-moisture exchanger device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention Like reference characters used therein indicate like parts throughout the several drawings.

DESCRIPTION OF THE INVENTION

Figure 1:
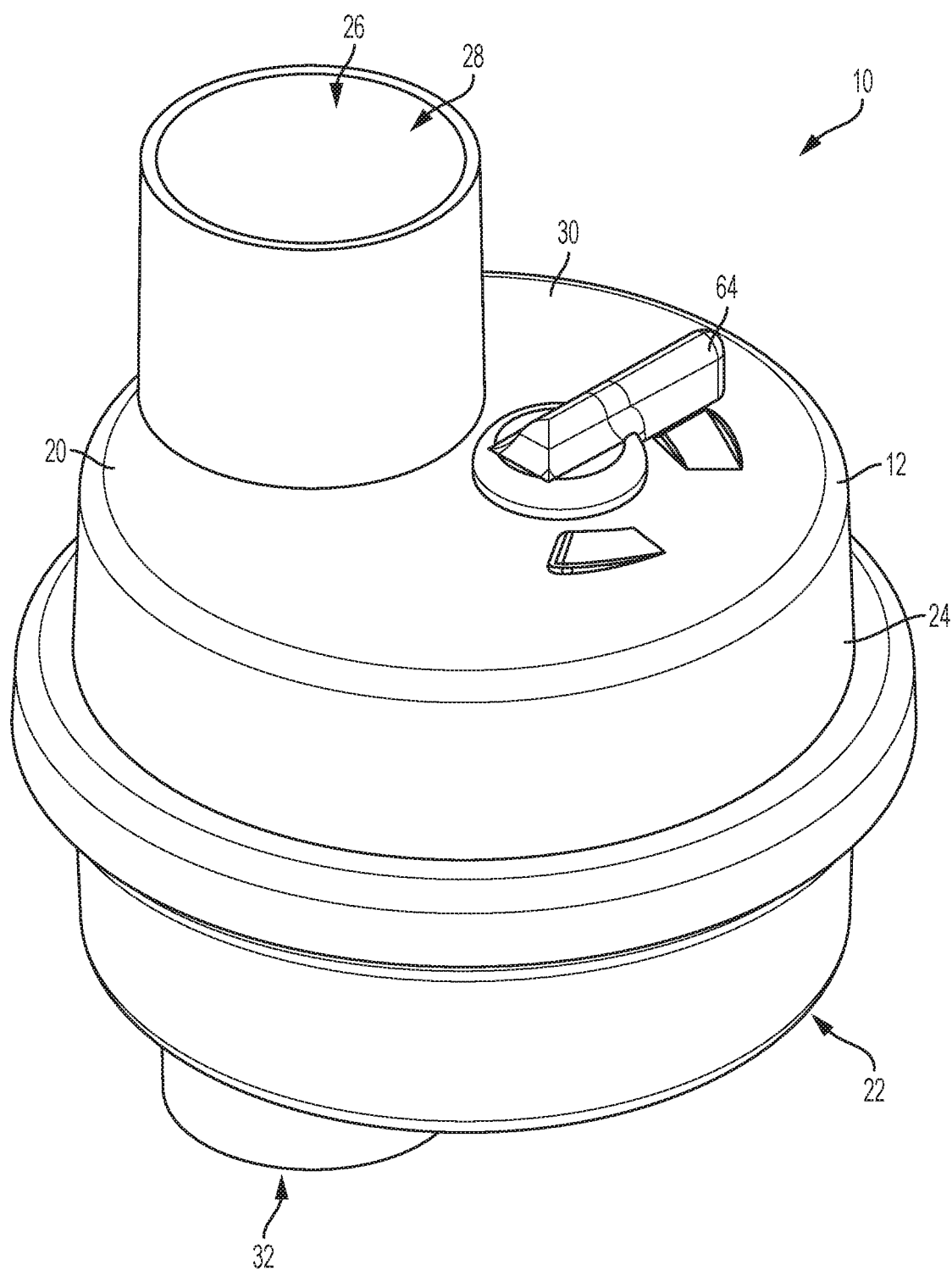
FIG. 1 is a perspective view of a heat-moisture exchanger device of the present application, according to one aspect.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "conduit" includes aspects having two or more conduits unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Presented herein is a heat-moisture exchanger ("HME") attachable to a patient ventilator circuit. In one aspect, the HME can be selectively adjustable to permit medicament to pass through the HME without passing through internally mounted filters and without disconnection from the ventilator circuit.

With reference to FIGS. 1-4, the HME device 10 comprises at least one of a housing 12, a rotatable central element 14 positioned in the housing and a filter 16 coupled to the central element.

In one aspect, the housing 12 can define a chamber 18 configured to hold the rotatable central element 14. For example, the housing can comprise a first wall 20, an opposed second wall 22 and sidewall 24 extending between the first wall and the second wall such that the chamber is defined by the first wall, the second wall and the sidewall. In another aspect, the sidewall can be substantially circular. In a further aspect, a first conduit 26 having a longitudinal axis $A_1$ can be coupled to or formed integrally with an outer surface 30 of the first wall. In this aspect, a first passageway 28 can be defined through the first conduit and the first wall. Thus, the first passageway can lead inwardly through the first wall and into the chamber 18. Similarly, a second conduit 32 having a longitudinal axis $A_2$ can be coupled to or formed integrally with an outer surface 36 of the second wall. In this aspect, a second passageway 34 can be defined through the second conduit and the second wall. Thus, the second passageway can lead inwardly through the second wall 22 and into the chamber 18.

Figure 4:
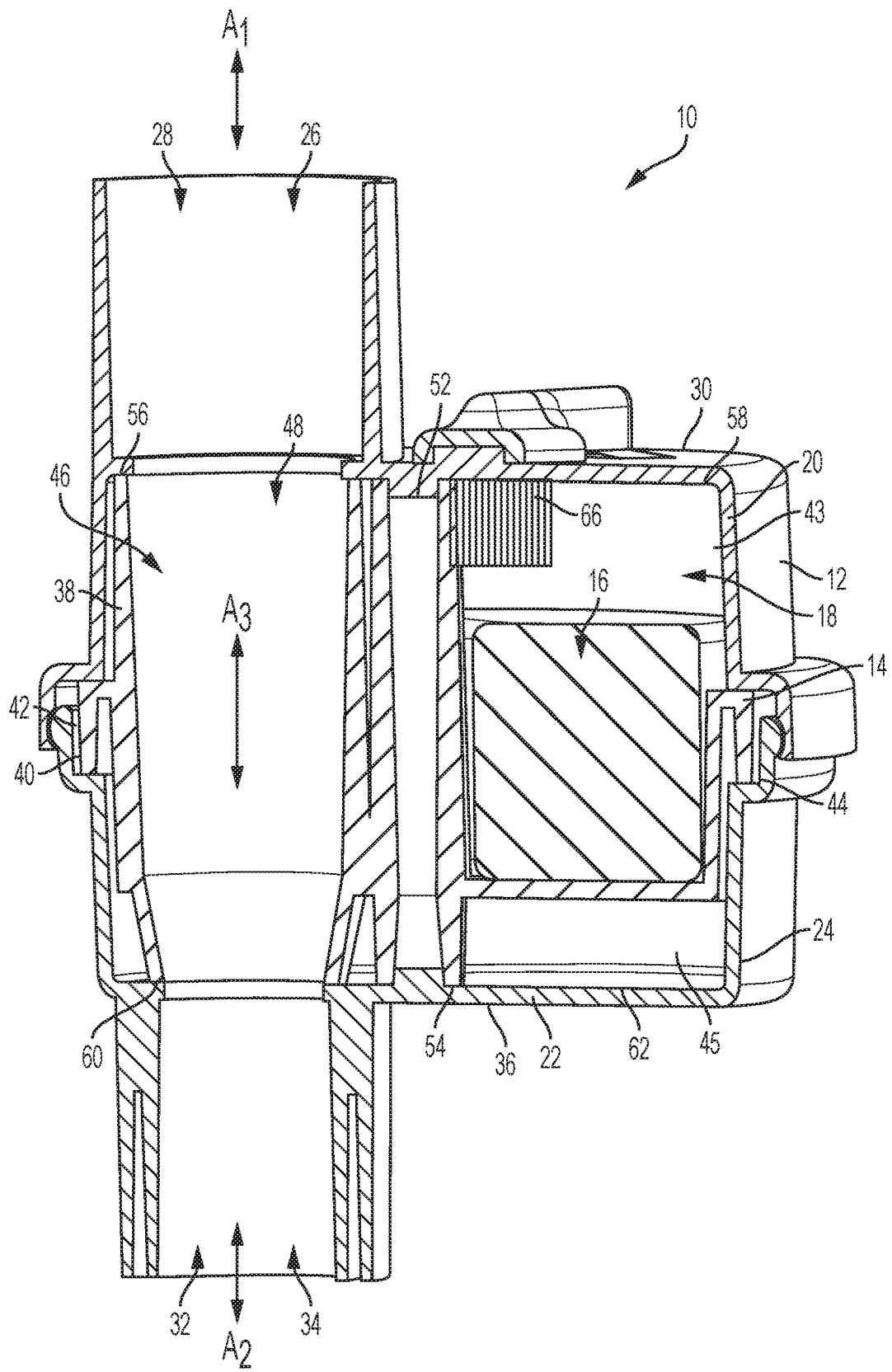
FIG. 4 is a cross-sectional view of the heat-moisture exchanger device of FIG. 3.

In one aspect, the longitudinal axis $A_1$ of the first conduit 26 can be substantially parallel to the longitudinal axis $A_2$ of the second conduit 32. Optionally, the longitudinal axis $A_1$ of the first conduit 26 can be at an acute angle relative to the longitudinal axis $A_2$ of the second conduit 32. As illustrated in FIG. 4, the first conduit can be positioned so that it is coaxially aligned with the second conduit 32. That is, the longitudinal axis $A_1$ of the first conduit can be substantially coaxially aligned with the longitudinal axis $A_2$ of the second conduit.

An inner diameter of the first conduit 26 can be substantially constant along the longitudinal axis $A_1$. Optionally, the inner diameter of the first conduit can get larger or smaller as the longitudinal distance from the inner diameter to the first wall 20 changes. That is, the inner diameter of the first conduit 26 can taper towards or away from the first wall. An inner diameter of the second conduit 32 can be substantially constant along the longitudinal axis $A_2$. Optionally, the inner diameter of the second conduit can get larger or smaller as the distance from the inner diameter to the second wall 22 changes. That is, the inner diameter of the second conduit 32 can taper towards or away from the second wall.

Referring now to FIG. 4, the rotatable central element 14 can be positioned in the chamber 18 of the housing 12. In one aspect, the rotatable central element comprises a body 38 configured to hold at least a portion of the filter 16. In another aspect, an outer edge 40 of the body can be sized and shaped to conform to, contact and/or engage at least a portion of an inner surface 42 of the sidewall 24 of the housing 12. For example, if the sidewall is substantially circular, the outer edge of the body can be substantially circular as well. In this aspect, when assembled, a fluid-tight seal can be formed between the outer edge of the body and the inner surface of the sidewall so that fluid cannot pass between the outer edge 40 of the body 38 and the inner surface 42 of the sidewall 24. Thus, the body can separate the chamber 18 of the housing into a first chamber 43 on one side of the body 38 and a second chamber 45 spaced from the first chamber on the opposed side of the body. Optionally, the seal between the outer edge of the body and the inner surface of the sidewall can be substantially fluid-tight, or slightly fluid-tight. In still another aspect, a shoulder 44 can be formed in the sidewall 24 to provide a support for a portion of the body 38 and/or to assist in forming the fluid-tight seal.

In one aspect, a third conduit 46 can be coupled to or formed integrally with a portion of the body 38 of the rotatable central element 14. In this aspect, the third conduit can extend from a first side 52 of the body to a second side 54 of the body. In another aspect, a third passageway 48 can be defined through the third conduit and an aperture defined in a portion of the body. Thus, the third conduit 46 can place the first side 52 of the body 38 in fluid communication with the second side 54 of the body. An inner diameter of the third conduit 46 can be substantially constant along a longitudinal axis $A_3$ of the third conduit. Optionally, the inner diameter of the third conduit 46 can get larger or smaller while extending from the first side 52 to the second side 54 of the body 38.

In one aspect, the third conduit 46 can have a length that corresponds to the distance between the first wall 20 and the second wall 22 of the housing 12. In this aspect, when assembled, a fluid-tight seal can be formed between a distal end 56 of the third conduit 46 and an inner surface 58 of the first wall so that fluid cannot pass between the distal end of the third conduit and the inner surface of the first wall 20. Similarly, a fluid-tight seal can be formed between a proximal end 60 of the third conduit 46 and an inner surface 62 of the second wall 22 so that fluid cannot pass between the distal end of the third conduit and the inner surface of the second wall. Optionally, the seal between the third conduit 46 and the first and/or second walls can be substantially fluid-tight, or slightly fluid-tight. As can be appreciated then, when the third conduit is aligned with the first conduit 26 and/or the second conduit 32, fluid can smoothly flow through the first passageway 28, the second passageway 34 and the third passageway 48 with negligible or little loss of fluid through the seals formed between the ends of the third conduit and the inner surface 58, 62 of the first and second walls. Similarly, when the third conduit 46 is not aligned with the first conduit 26 and/or the second conduit the seals formed between the ends of the third conduit 46 and the inner surface of the first and second walls can prevent fluid from flowing through the third passageway 48.

Figure 3:
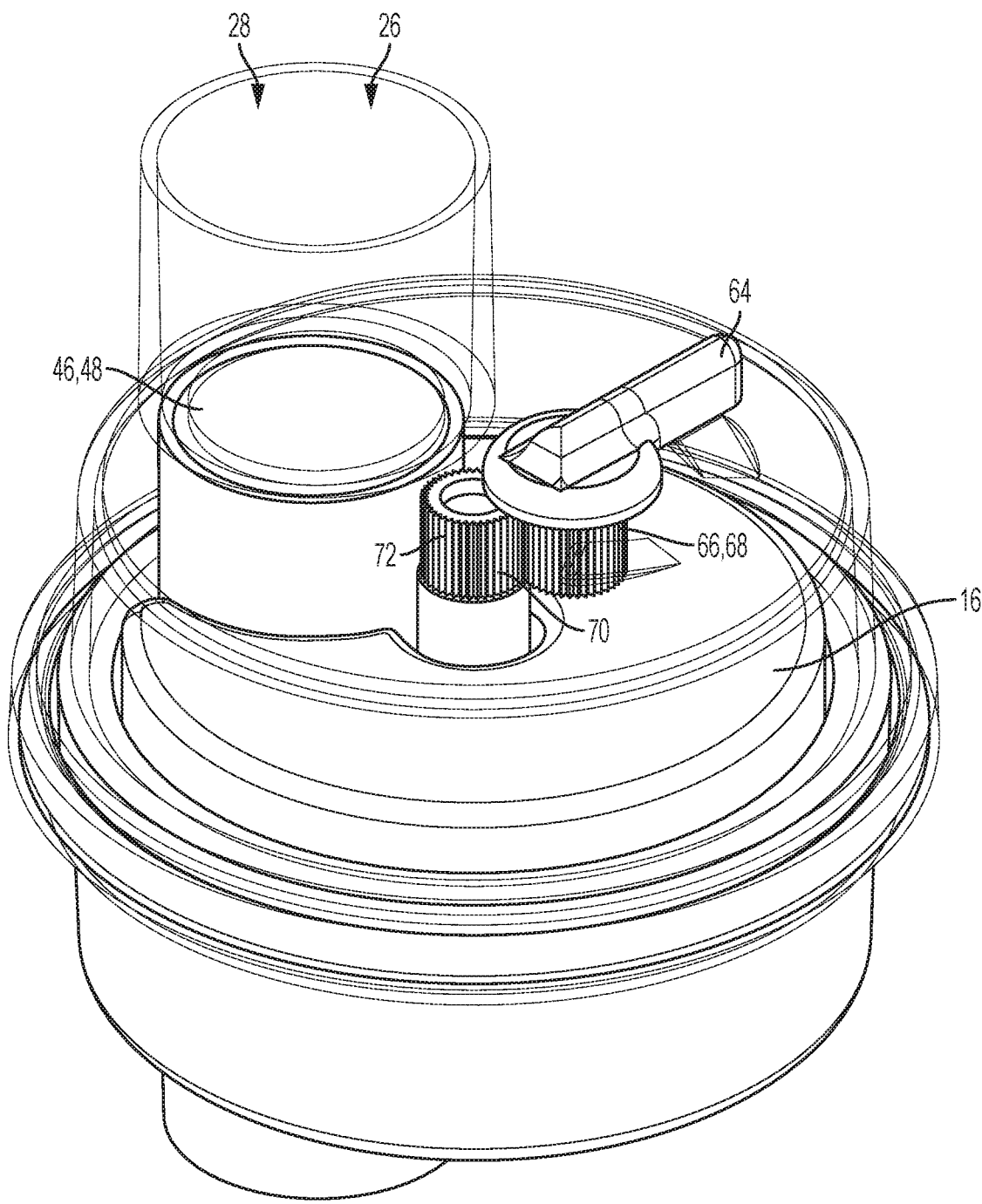
FIG. 3 is a perspective view of the heat-moisture exchanger device of FIG. 1, in which a portion of the housing of the heat-moisture exchanger device is illustrated transparently for clarity, and in which the rotatable central element is in a first, open position.

In one aspect, the rotatable central element can rotate about and between a first position, in which the longitudinal axis $A_3$ of the third conduit 46 is substantially aligned with at least one of the longitudinal axis $A_1$ of the first conduit 26 and the longitudinal axis $A_2$ of the second conduit 32, and a second position, in which the longitudinal axis $A_3$ of the third conduit is not aligned with at least one of the longitudinal axis $A_1$ of the first conduit and the longitudinal axis $A_2$ of the second conduit. As illustrated in FIGS. 3 and 4, in the first position, the first passageway 28, the second passageway 34 and the third passageway 48 can be substantially aligned longitudinally so that fluid can smoothly flow through the aligned passageways. In another aspect, in the first position, the third conduit 46 can selectively place the first conduit 26 in sealed fluid communication with the second conduit 32 (bypassing the filter 16).

Figure 2:
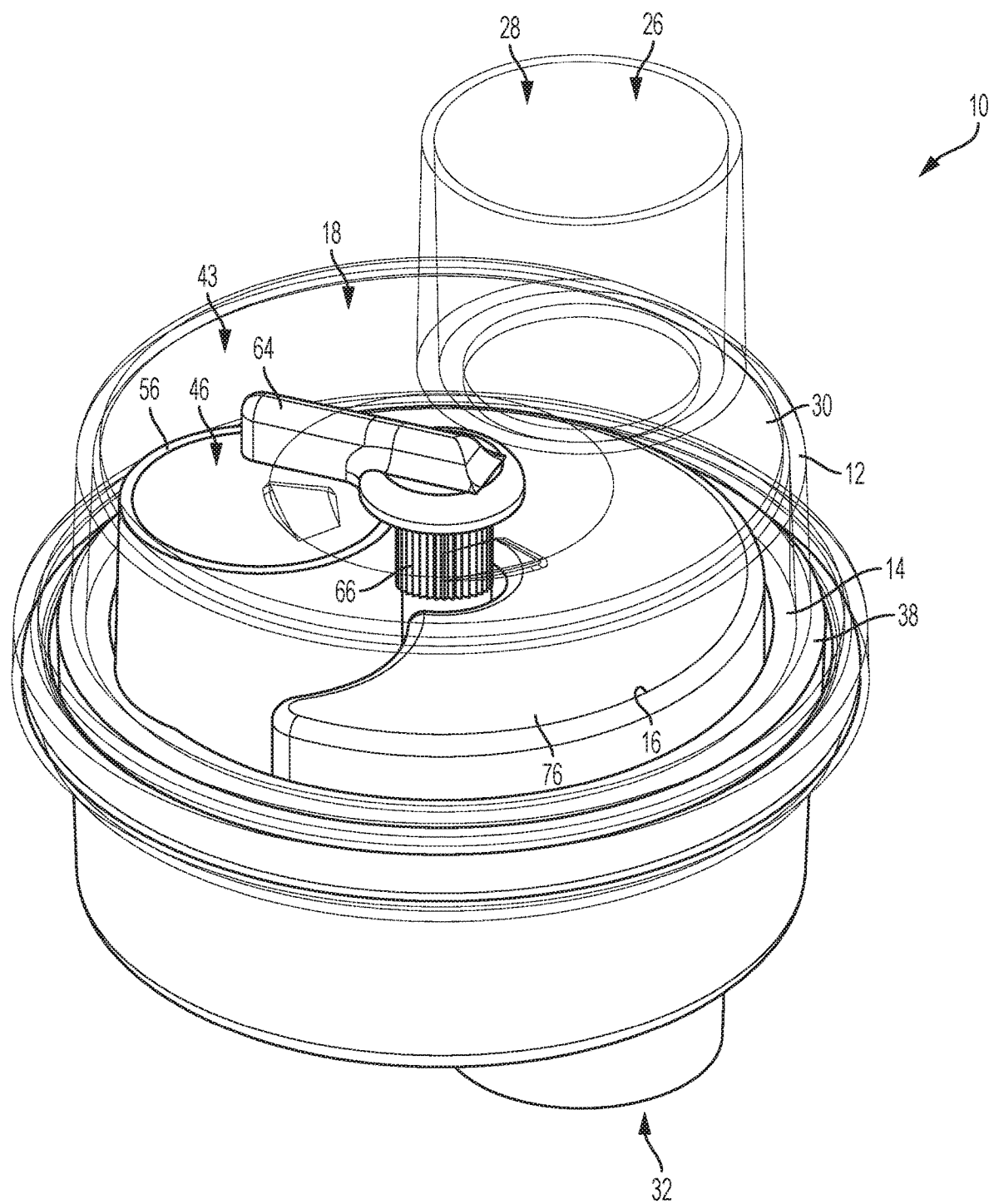
FIG. 2 is a perspective view of the heat-moisture exchanger device of FIG. 1, in which a portion of a housing of the heat-moisture exchanger device is illustrated transparently for clarity, and in which a rotatable central element of the heat-moisture exchanger device is in a second, closed position.

Further, in the second position, the first passageway 28, the second passageway 34 and the third passageway 48 can be misaligned so that fluid will not flow smoothly through the passageways. In one aspect, and as illustrated in FIG. 2, in the second position, the distal end 56 of the third conduit 46 can contact and/or engage the inner surface 58 of the first wall 20 to form a seal and substantially prevent the flow of fluid between the first passageway and the third passageway. In another aspect, in the second position, the proximal end 60 of the third conduit can contact and/or engage the inner surface 62 of the second wall to form a seal and substantially prevent the flow of fluid between the second passageway and the third passageway 48. Thus, in the second position, any fluid entering the chamber 18 through the first passageway 28 must pass through the filter 16 in order to exit the chamber through the second passageway 34, and any fluid entering the chamber 18 through the second passageway must pass through the filter in order to exit the chamber through the first passageway. In another aspect, in the second position, the filter 16 can be positioned between the first conduit 26 and the second conduit 32.

The rotatable central element 14 can further comprise a means for rotating the central element relative to the housing 12. For example, the rotatable central element 14 can further comprise a handle 64 extending through the first wall 20, wherein the handle is coupled to the body 38 so that rotation of the handle causes the body to rotate relative to the housing. In one aspect, the rotatable central element 14 can further comprise a plurality of gears 66. For example, a first gear 68 can be coupled to or formed integrally with the handle 64 and a second gear 70 can be coupled to or formed integrally with a portion of the body 38. Teeth 72 defined in the first gear can interlock with teeth defined in the second gear such that rotation of the first gear 68 can cause corresponding rotation of the second gear 70.

The filter 16 can be a heat-moisture exchange material 76 ("HMEM"), according to one aspect. The HMEM can be positioned in at least a portion of the body 38 of the rotatable central element 14. In another aspect, the HMEM can be sized and shaped so that when assembled, fluid moving from the first chamber 43 to the second chamber 45 must pass through the HMEM. That is, when the use of the HMEM is desired, the HME device 10 merely needs to have the rotatable central element 14 rotated to the second position as shown in FIG. 2. In this position, air and moisture from or to the patient must pass through the HMEM.

The components shown above except for the heat-moisture exchange material 76 can be made from a rigid high strength plastic such as polypropylene, polyethylene, polyamide, polycarbonate and the like. The HMEM 76 can be obtained from, for example and without limitation, polyurethane foam coated in a sodium chloride solution.

In use, when the rotatable central element 14 is in the first position, the third conduit 46 can be aligned with the first conduit 26 and/or the second conduit 32 and fluid can smoothly flow through the first passageway 28, the second passageway 34 and the third passageway 48 with negligible or little loss of fluid through the seal formed between the ends of the third conduit and the inner surface 58, 62 of the first and second walls. This first position can be used, for example, to allow for medication to flow directly through the HME device without passing through the filter 16. When the rotatable central element 14 is in the second position, the seal formed between the ends of the third conduit 46 and the inner surface of the first and second walls can prevent fluid from flowing through the third passageway 48. Thus, any fluid flowing into the first passageway 28 must pass through the filter to reach the second passageway 34 and exit the chamber 18, and any fluid flowing into the second passageway must pass through the filter 16 to reach the first passageway and exit the chamber. This second position can be used, for example, when it is desirable to capture heat and moisture exhaled from a patient.

By attaching the first conduit 26 of the HME device 10 of this application to a patient ventilation system, and the second conduit to an aerosol generator, such as a nebulizer, the normal continuity of the exchanger circuit is not interrupted. Instead, the HME device allows for entry of an aerosolized liquid medication from an aerosol generator, merely by turning the rotatable central element 14 to longitudinally align the first, second and third passageways. For example, a tube can connect the aerosol generator to the first conduit 26. With the passageways aligned, the absorbent HMEM 76 is by-passed. The HME device 10 maintains the continuity of a closed ventilator circuit without interruption of the ventilation circuit to a patient.

The HME device 10 as described herein can allow for entry of medication to the patient ventilation circuit without requiring the medication to pass through turns or past obstructions such as fan blades and the like. Instead, the medication can pass smoothly through the first second and third passageways when the passageways are aligned. Further, the HME device of the present application can be made inexpensively and thus can be disposed of after use.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings.

It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A heat-moisture exchanger device for use with a patient ventilator circuit, the heat-moisture exchanger device comprising:
   a housing comprising a first wall, an opposed second wall and sidewall extending between the first wall and the second wall such that a chamber is defined by the first wall, the second wall and the sidewall, wherein a first conduit is positioned thereon an outer surface of the first wall, wherein a first passageway is defined through the first conduit and the first wall, wherein a second conduit is positioned thereon an outer surface of the second wall, wherein a second passageway is defined through the second conduit and the second wall, and wherein a longitudinal axis of the first conduit and a longitudinal axis of the second conduit are substantially aligned;
   a rotatable central element positioned in the chamber of the housing, wherein the rotatable central element comprises a body, wherein a third conduit having a longitudinal axis is positioned thereon the body, wherein the third conduit extends from a first side of the body to a second side of the body, and wherein a third passageway is defined through the third conduit; and
   a filter coupled to and rotatable with the rotatable central element,
   wherein the rotatable central element is rotatable about and between a first position, in which the longitudinal axis of the third conduit is substantially aligned with the longitudinal axis of the first conduit and the longitudinal axis of the second conduit, and a second position, in which the longitudinal axis of the third conduit is not aligned with the longitudinal axis of the first conduit and is not aligned with the longitudinal axis of the second conduit,
   wherein the rotatable central element further comprises a handle extending through the first wall, and wherein the handle is coupled to the body such that rotation of the handle causes the body to rotate relative to the housing, wherein rotation of the handle causes the rotatable central element to rotate about and between the first position and the second position,
   wherein the rotatable central element further comprises a plurality of gears, wherein a first gear of the plurality of gears is coupled to the handle and a second gear of the plurality of gears is coupled to the body, and wherein teeth defined in the first gear interlock with teeth defined in the second gear such that rotation of the first gear causes corresponding rotation of the second gear.

2. The heat-moisture exchanger device of claim 1, wherein an inner diameter of the first conduit decreases as the longitudinal distance from the inner diameter to the first wall decreases.

3. The heat-moisture exchanger device of claim 1, wherein an inner diameter of the second conduit increases as the longitudinal distance from the inner diameter to the second wall increases.

4. The heat-moisture exchanger device of claim 1, wherein the longitudinal axis of the first conduit is substantially parallel to the longitudinal axis of the second conduit.

5. The heat-moisture exchanger device of claim 1, wherein the body is configured to hold at least a portion of the filter.

6. The heat-moisture exchanger device of claim 1, wherein an outer edge of the body engages at least a portion of an inner surface of the sidewall of the housing, and wherein the engagement between the outer edge of the body and at least a portion of the inner surface of the sidewall forms a substantially fluid-tight seal.

7. The heat-moisture exchanger device of claim 1, wherein the third conduit has a length that corresponds to the distance between an inner surface of the first wall and an inner surface of the second wall.

8. The heat-moisture exchanger device of claim 7, wherein a substantially fluid-tight seal is formed between a distal end of the third conduit and the inner surface of the first wall, and wherein a substantially fluid-tight seal is formed between a proximal end of the third conduit and the inner surface of the second wall.

9. The heat-moisture exchanger device of claim 8, wherein in the first position, fluid flows smoothly through the first passageway, the second passageway and the third passageway without loss of fluid from the passageways through the seal formed between the distal end of the third conduit and the inner surface of the first wall.

10. The heat-moisture exchanger device of claim 9, wherein in the second position, fluid flows through the first passageway and the second passageway without loss of fluid from the chamber through the seal formed between the distal end of the third conduit and the inner surface of the first wall.

11. The heat-moisture exchanger device of claim 10, wherein in the second position, the filter is positioned between the first passageway and the second passageway.

12. The heat-moisture exchanger device of claim 1, wherein the filter is a heat-moisture exchange material.

13. The heat-moisture exchanger device of claim 12, wherein the heat-moisture exchange material is sized and shaped so that in the second position, fluid moving between the first and second passageways must pass through the heat-moisture exchange material.

14. The heat-moisture exchanger device of claim 1, wherein the first conduit is attachable to an aerosol generator, and wherein the second conduit is attachable to a patient ventilation system.

15. The heat-moisture exchanger device of claim 1, wherein, in the first position, the filter is neither aligned with the longitudinal axis of the first conduit nor the longitudinal axis of the second conduit.

16. A method for inputting an aerosolized medication into a patient ventilation system without interrupting the normal continuity of the system, the method comprising:

providing a heat-moisture exchanger device comprising:

a housing comprising a first wall, an opposed second wall and sidewall extending between the first wall and the second wall such that a chamber is defined by the first wall, the second wall and the sidewall, wherein a first conduit is positioned thereon an outer surface of the first wall, wherein a first passageway is defined through the first conduit and the first wall, wherein a second conduit is positioned thereon an outer surface of the second wall, wherein a second passageway is defined through the second conduit and the second wall, and wherein a longitudinal axis of the first conduit and a longitudinal axis of the second conduit are substantially aligned;

a rotatable central element positioned therein the chamber of the housing, wherein the rotatable central element comprises a body, wherein an outer edge of the body engages at least a portion of an inner surface of the sidewall of the housing, wherein a third conduit having a longitudinal axis is positioned thereon the body, wherein the third conduit extends from a first side of the body to a second side of the body, and wherein a third passageway is defined through the third conduit; and a filter coupled to and rotatable with the rotatable central element wherein the rotatable central element further comprises a handle extending through the first wall, and wherein the handle is coupled to the body such that rotation of the handle causes the body to rotate relative to the housing, wherein rotation of the handle causes the rotatable central element to rotate about and between the first position and the second position, wherein the rotatable central element further comprises a plurality of gears, wherein a first gear of the plurality of gears is coupled to the handle and a second gear of the plurality of gears is coupled to the body, and wherein teeth defined in the first gear interlock with teeth defined in the second gear such that rotation of the first gear causes corresponding rotation of the second gear;

attaching the first conduit to an aerosol generator, and the second conduit to the patient ventilation system;

rotating the rotatable central element from a second position, in which fluid flows through the filter, to a first position in which the longitudinal axis of the third conduit is substantially aligned with the longitudinal axis of the first conduit and the longitudinal axis of the second conduit;

inputting the aerosolized medication from the aerosol generator through the first conduit; and rotating the rotatable central element to the first position after the medication has been input.

17. A heat-moisture exchanger device for use with a patient ventilator circuit, the heat-moisture exchanger device comprising:

a housing comprising a first wall, an opposed second wall, and a sidewall extending between the first wall and the second wall such that a chamber is defined by the first wall, the second wall, and the sidewall, wherein a first conduit is positioned on an outer surface of the first wall, wherein a first passageway is defined through the first conduit and the first wall, wherein a second conduit is positioned on an outer surface of the second wall, wherein a second passageway is defined through the second conduit and the second wall, and wherein a longitudinal axis of the first conduit and a longitudinal axis of the second conduit are substantially aligned;

a rotatable central element positioned in the chamber of the housing, wherein the rotatable central element comprises a body, wherein a third conduit having a longitudinal axis is positioned thereon the body, wherein the third conduit extends from a first side of the body to a second side of the body, and wherein a third passageway is defined through the third conduit; and a filter coupled to the rotatable central element, wherein the rotatable central element is rotatable about and between a first position, in which the longitudinal axis of the third conduit is substantially aligned with the longitudinal axis of the first conduit and the longitudinal axis of the second conduit, and a second position, in which the longitudinal axis of the third conduit is not aligned with the longitudinal axis of the first conduit or the longitudinal axis of the second conduit, wherein, in the first position, the filter is neither aligned with the longitudinal axis of the first conduit nor the longitudinal axis of the second conduit wherein the rotatable central element further comprises a handle extending through the first wall, and wherein the handle is coupled to the body such that rotation of the handle causes the body to rotate relative to the housing, wherein rotation of the handle causes the rotatable central element to rotate about and between the first position and the second position, wherein the rotatable central element further comprises a plurality of gears, wherein a first gear of the plurality of gears is coupled to the handle and a second gear of the plurality of gears is coupled to the body, and wherein teeth defined in the first gear interlock with teeth defined in the second gear such that rotation of the first gear causes corresponding rotation of the second gear.

* * * * *